US00PP22012P3

(12) United States Plant Patent
Tuinier

(10) Patent No.: US PP22,012 P3
(45) Date of Patent: Jul. 5, 2011

(54) ***ALOE×GASTERIA* PLANT NAMED 'WT01'**

(50) Latin Name: ***Aloe×Gasteria* hybrid**
Varietal Denomination: WT01

(76) Inventor: Wander Tuinier, Krimpen a/d IJssel (NL)

( * ) Notice: Subject to any disclaimer, the term of this patent is extended or adjusted under 35 U.S.C. 154(b) by 0 days.

(21) Appl. No.: 12/589,200

(22) Filed: Oct. 19, 2009

(65) Prior Publication Data

US 2011/0093993 P1 Apr. 21, 2011

(51) Int. Cl.
*A01H 5/00* (2006.01)

(52) U.S. Cl. ..... Plt./373

(58) Field of Classification Search ..... Plt./373
See application file for complete search history.

*Primary Examiner* — June Hwu
*Assistant Examiner* — Louanne C Krawczerwicz Myers

(57) ABSTRACT

A new and distinct *Aloe×Gasteria* hybrid cultivar named 'WT01' is disclosed, characterized by durable foliage, resistant to breakage and a faster growth habit than similar species. The new variety is a *Aloe×Gasteria* hybrid, typically produced as an ornamental plant.

1 Drawing Sheet

Figure 1:
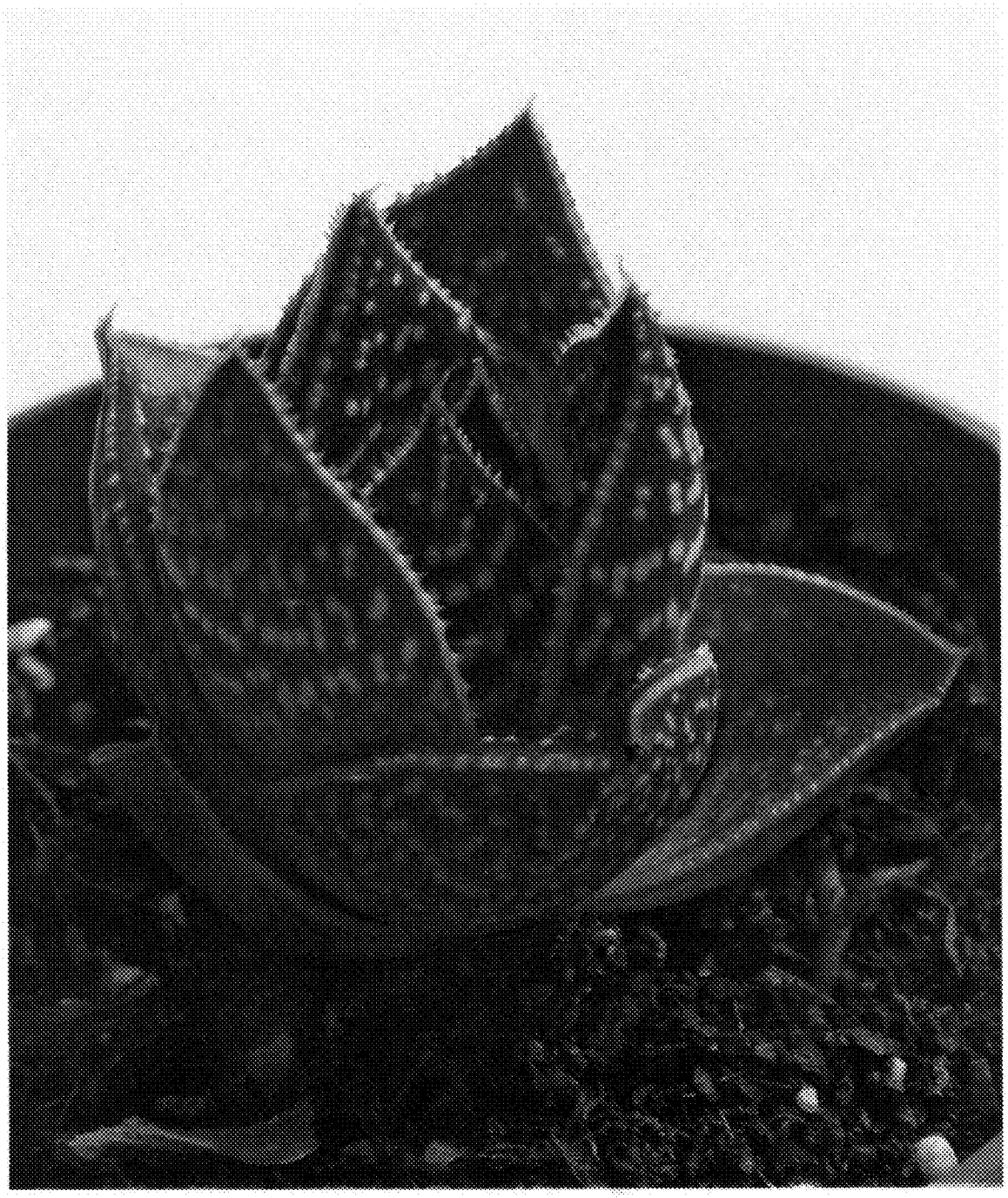

Latin name of the genus and species: *Aloe×Gasteria* hybrid.

Variety denomination: 'WT01'.

BACKGROUND OF THE INVENTION

The new cultivar was discovered as a seedling, resulting from the planned crossing of an unnamed *Aloe* hybrid(unpatented) as the seed parent and an, unnamed, unpatented *Gasteria*, nitida as the pollen parent 'WT01' was discovered by the inventor, Wander Durk Tuinier, a citizen of the Netherlands, in a group of seedlings resulting from the aforementioned crossing. The new variety was discovered September 2007, in a commercial greenhouse in Swellendam, South Africa.

Asexual reproduction of the new cultivar 'WT01' was first performed in South Africa, in Swellendam at a commercial laboratory by tissue culture in January 2008. 'WT01' has since produced several generations and has shown that the unique features of this cultivar are stable and reproduced true to type.

SUMMARY OF THE INVENTION

The cultivar 'WT01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WT01.' These characteristics in combination distinguish 'WT01' as a new and distinct *Aloe×Gasteria* cultivar:

1. Strong, durable foliage, resistant to rot and breakage.
2. Fast, vigorous growth rate.

PARENTAL COMPARISON

Plants of the new cultivar 'WT01' are similar to plants of the unnamed seed parent variety in most horticultural characteristics. However, plants of the new cultivar 'WT01' produce foliage that is more resistant to rot and breakage. Additionally, the new cultivar produces a much less regular rosette type plant shape. The new cultivar has leaves that are close to an opposite rosetting arrangement, as compared to the whorled rosette of the seed parent.

Plants of the new cultivar 'WT01' are similar to plant of the unknown *Gasteria* pollen parent in most horticultural characteristics. However, plants of the new cultivar 'WT01' are much faster growing than the pollen parent.

COMMERCIAL COMPARISON

Plants of 'WT01' can be compared to the known commercial variety, *Aloe aristata*(unpatented). Differences are similar to those with the seed parent. 'WT01' produces stronger, more durable foliage than *Aloe aristata*. Additionally, the new cultivar exhibits a more opposite rosette leaf pattern than a tightly held whorled rosette as seen in *Aloe aristata*.

BRIEF DESCRIPTION OF THE PHOTOGRAPH

The accompanying photograph in FIG. 1 illustrates in full color a typical plant of 'WT01' indoors in the Netherlands. This plant is approximately 5 months old, shown in a 4 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The R.H.S. Colour Chart, except where general terms of ordinary dictionary significance are used. The following observations and measurements describe 'WT01' plants in a commercial greenhouse in Kimpen aan de Ijssel, the Netherlands. Temperatures ranged from 20° C. to 22° C. night and day. No artificial light, photoperiodic treatments or chemical treatments were given to the plants. Measurements and numerical values represent averages of typical plant types.

Botanical classification: *Aloe×Gasteria* hybrid 'WT01.'

Age of the plant described: Approximately 5 months.

PROPAGATION

Time to initiate roots: Approximately 20 to 25 days at 21° C.
Root description: Fibrous.
Propagation method: Tissue culture.

PLANT

Growth habit: Compact succulent.
Container size: 4 inch.
Height: Approximately 4.5 cm.
Plant spread: Approximately 3.9 cm.
Growth rate: Moderate to slow, approximately 0.5 cm per month.
Branching characteristics: Non-branching, no stems or lateral branches. To date, only a single basal rosette of leaves has been observed.

FOLIAGE

Leaf:

*Arrangement.*—Rosulate, simple leaf.
*Average quantity of leaves per rosette.*—Approximately 10.
*Average length.*—Approximately 4.1 cm.
*Widest width.*—Approximately 2.2 cm.
*Height/thickness.*—Approximately 0.4 cm.
*Shape of blade.*—Subulate.
*Apex.*—Acuminate.
*Base.*—Broad cuneate.
*Margin.*—Finely serrate.
*Texture of top surface.*—Rough, dull, non-pubescent.
*Texture of bottom surface.*—Rough, dull, non-pubescent.
*Color.*—Young foliage upper side: Near RHS Green N137A, mid-section lighter; near Green 143C, base near Yellow-Green 145D. Leaf covered with axillary rows of small dots, colored near White N155C, dots very small, average width: 0.8 mm in diameter. Young foliage under side: Near RHS Green N137A, mid-section lighter; near Green 143C, base near Yellow-Green 145D. Leaf covered with axillary rows of small dots, colored near White N155C, dots very small, average width: 0.8 mm in diameter. Mature foliage upper side: Near RHS Green N137A, lower half near Green-White; 157B Upper half of leaf covered with axillary rows of small dots, colored white, near N155C, dots very small, average width: 0.8 mm in diameter. Mature foliage under side: Near RHS Green N137A, mid-section near Yellow-Green 146D, base Green-White 157A. Leaf covered with axillary rows of small dots, colored white near N155C, dots very small, average width: 0.8 mm in diameter.
*Venation.*—Veination not visible.
*Petiole.*—No petiole.

Other characteristics: Foliage highly resistant to tearing or breaking due to mechanical stress. No stipules, tendrils, thorns, or spines present.

FLOWER

Bud production and flower production has not been observed to date.

REPRODUCTIVE ORGANS

Not observed due to lack of flower production.

OTHER CHARACTERISTICS

Disease resistance: Neither resistance nor susceptibility to diseases or pests has been observed in this variety.
Drought tolerance and temperature tolerance: Drought tolerant succulent. Low temperature tolerance to at least USDA Zone 10. Tolerates high temperature to at least 45° C.
Fruit/seed production: Fruits and seeds have not been observed to date.

What is claimed is:

1. A new and distinct cultivar of *Aloe×Gasteria* hybrid plant named 'WT01' as herein illustrated and described.

* * * * *